(12) United States Patent
Kern et al.

(10) Patent No.: US 7,994,096 B2
(45) Date of Patent: Aug. 9, 2011

(54) METHOD FOR ANTIGEN-SPECIFIC STIMULATION OF T LYMPHOCYTES WITH SYNTHETIC PEPTIDE LIBRARIES

(76) Inventors: Florian Kern, Berlin (DE); Hans-Dieter Volk, Berlin (DE); Petra Reinke, Berlin (DE); Nicole Faulhaber, Rheurdt (DE); Ingolf-Pascal Surel, Berlin (DE); Elham Khatamzas, Berlin (DE)

( * ) Notice: Subject to any disclaimer, the term of this patent is extended or adjusted under 35 U.S.C. 154(b) by 0 days.

(21) Appl. No.: 10/203,915

(22) PCT Filed: Feb. 17, 2001

(86) PCT No.: PCT/EP01/01773
§ 371 (c)(1),
(2), (4) Date: Mar. 17, 2003

(87) PCT Pub. No.: WO01/63286
PCT Pub. Date: Aug. 30, 2001

(65) Prior Publication Data
US 2004/0110240 A1 Jun. 10, 2004

(30) Foreign Application Priority Data

Feb. 22, 2000 (DE) .................. 100 09 341

(51) Int. Cl.
*C40B 30/04* (2006.01)
*C07H 81/04* (2006.01)
(52) U.S. Cl. ............. 506/9; 435/7.21; 435/7.2; 435/7.1; 435/4; 506/7
(58) Field of Classification Search ............. 435/7.1, 435/4, DIG. 15, DIG. 14, DIG. 35, 6, 7.21, 435/7.2; 530/350, 324; 506/7, 9
See application file for complete search history.

(56) References Cited

U.S. PATENT DOCUMENTS 5,866,344 A * 2/1999 Georgiou ............. 435/7.21
6,207,161 B1 * 3/2001 Pande et al. ........... 424/186.1
6,355,479 B1 * 3/2002 Webb et al. ............. 435/325

FOREIGN PATENT DOCUMENTS

WO WO 98/15833 * 4/1998

OTHER PUBLICATIONS ou et al , Human Immunology, 1999, 60(8), 652-64.*
Harris et al, International Immunology, 1997, 9(2), 273-280.*
Carballido et al, The Jrnl. of Immunology, 150, 3582-3591(8), 1993.*
Harris, Stephen J; "Prediction of murine MHC class I epitopes in a major house dust mite allergen and induction of T1-type CD8+ cell responses"; 1997, Oxford University Press; pp. 273-280; International Immunology, vol. 9, No. 2.
Ou, Dawei, et al; CD4+ and CD8– T-Cell Clones from Congenital Rubellia Sundrome Patients with IDDM Recognize Overlapping GAD65 Protein Epitopes: Implications for HL Class I and II Allelic Linkage to Disease Susceptibility; 1999, Human Immunology, pp. 652-664, Vol. 60C.

* cited by examiner

*Primary Examiner* — T. D. Wessendorf
(74) *Attorney, Agent, or Firm* — Norris McLaughlin & Marcus, P.A.

(57) ABSTRACT

The invention relates to a method for the antigen-specific stimulation of T-lymphocytes with a synthetic peptide library, by preparing a plurality of peptides, each of said peptides comprising a fragment less than the whole of the total amino acid sequence of the antigen, each of said peptides being a minimum of 9 amino acid residues (AAs) in length, and the amino acid sequence of each peptide overlapping with the amino acid sequence of at least one other of said peptides; combining a plurality of the peptides from a) into a peptide library, said peptide library comprises a plurality of the peptides selected such that their collective overlapping amino acid sequences span the total amino acid sequence of the antigen; and incubating a suspension comprising CD8+ T lymphocytes, CD4+ T lymphocytes or a mixture of CD8+ and CD4+ with said peptide library in a single culture run.

13 Claims, 3 Drawing Sheets

Fig. 1

| # | Sequence | # | Sequence | # | Sequence |
|---|---|---|---|---|---|
| 1. | MESSAKRKMDPDNPD | 41. | EDKREMWMACIKELH | 81. | SVMLAKRPLITKPEV |
| 2. | AKRKMDPDNPDEGPS | 42. | EMWMACIKELHDVSK | 82. | AKRPLITKPEVISVM |
| 3. | MDPDNPDEGPSSKVP | 43. | ACIKELHDVSKGAAN | 83. | LITKPEVISVMKRRI |
| 4. | NPDEGPSSKVPRPET | 44. | ELHDVSKGAANKLGG | 84. | PEVISVMKRRIEEIC |
| 5. | GPSSKVPRPETPVTK | 45. | VSKGAANKLGGALQA | 85. | SVMKRRIEEICMKVF |
| 6. | KVPRPETPVTKATTF | 46. | AANKLGGALQAKARA | 86. | RRIEEICMKVFAQYI |
| 7. | PETPVTKATTFLQTM | 47. | LGGALQAKARAKKDE | 87. | EICMKVFAQYILGAD |
| 8. | VTKATTFLQTMLRKE | 48. | LQAKARAKKDELRRK | 88. | KVFAQYILGADPLRV |
| 9. | TTFLQTMLRKEVNSQ | 49. | ARAKKDELRRKMMYM | 89. | QYILGADPLRVCSPS |
| 10. | QTMLRKEVNSQLSLG | 50. | KDELRRKMMYMCYRN | 90. | GADPLRVCSPSVDDL |
| 11. | RKEVNSQLSLGDPLF | 51. | RRKMMYMCYRNIEFF | 91. | LRVCSPSVDDLRAIA |
| 12. | NSQLSLGDPLFPELA | 52. | MYMCYRNIEFFTKNS | 92. | SPSVDDLRAIAEESD |
| 13. | SLGDPLFPELAEESL | 53. | YRNIEFFTKNSAFPK | 93. | DDLRAIAEESDEEEA |
| 14. | PLFPELAEESLKTFE | 54. | EFFTKNSAFPKTTNG | 94. | AIAEESDEEEAIVAY |
| 15. | ELAEESLKTFEQVTE | 55. | KNSAFPKTTNGCSQA | 95. | ESDEEEAIVAYTLAT |
| 16. | ESLKTFEQVTEDCNE | 56. | FPKTTNGCSQAMAAL | 96. | EEAIVAYTLATAGVS |
| 17. | TFEQVTEDCNENPEK | 57. | TNGCSQAMAALQNLP | 97. | VAYTLATAGVSSSDS |
| 18. | VTEDCNENPEKDVLA | 58. | SQAMAALQNLPQCSP | 98. | LATAGVSSSDSLVSP |
| 19. | CNENPEKDVLAELVK | 59. | AALQNLPQCSPDEIM | 99. | GVSSSDSLVSPPESP |
| 20. | PEKDVLAELVKQIKV | 60. | NLPQCSPDEIMAYAQ | 100. | SDSLVSPPESPVPAT |
| 21. | VLAELVKQIKVRVDM | 61. | CSPDEIMAYAQKIFK | 101. | VSPPESPVPATIPLS |
| 22. | LVKQIKVRVDMVRHR | 62. | EIMAYAQKIFKILDE | 102. | ESPVPATIPLSSVIV |
| 23. | IKVRVDMVRHRIKEH | 63. | YAQKIFKILDEERDK | 103. | PATIPLSSVIVAENS |
| 24. | VDMVRHRIKEHMLKK | 64. | IFKILDEERDKVLTH | 104. | PLSSVIVAENSDQEE |
| 25. | RHRIKEHMLKKYTQT | 65. | LDEERDKVLTHIDHI | 105. | VIVAENSDQEESEQS |
| 26. | KEHMLKKYTQTEEKF | 66. | RDKVLTHIDHIFMDI | 106. | ENSDQEESEQSDEEE |
| 27. | LKKYTQTEEKFTGAF | 67. | LTHIDHIFMDILTTC | 107. | QEESEQSDEEEEEGA |
| 28. | TQTEEKFTGAFNMMG | 68. | DHIFMDILTTCVETM | 108. | EQSDEEEEEGAQEER |
| 29. | EKFTGAFNMMGGCLQ | 69. | MDILTTCVETMCNEY | 109. | EEEEGAQEEREDTV |
| 30. | GAFNMMGGCLQNALD | 70. | TTCVETMCNEYKVTS | 110. | EGAQEEREDTVSVKS |
| 31. | MMGGCLQNALDILDK | 71. | ETMCNEYKVTSDACM | 111. | EEREDTVSVKSEPVS |
| 32. | CLQNALDILDKVHEP | 72. | NEYKVTSDACMMTMY | 112. | DTVSVKSEPVSEIEE |
| 33. | ALDILDKVHEPFEEM | 73. | VTSDACMMTMYGGIS | 113. | VKSEPVSEIEEVAPE |
| 34. | LDKVHEPFEEMKCIG | 74. | ACMMTMYGGISLLSE | 114. | PVSEIEEVAPEEEED |
| 35. | HEPFEEMKCIGLTMQ | 75. | TMYGGISLLSEFCRV | 115. | IEEVAPEEEEDGAEE |
| 36. | EEMKCIGLTMQSMYE | 76. | GISLLSEFCRVLCCY | 116. | APEEEEDGAEEPTAS |
| 37. | CIGLTMQSMYENYIV | 77. | LSEFCRVLCCYVLEE | 117. | EEDGAEEPTASGGKS |
| 38. | TMQSMYENYIVPEDK | 78. | CRVLCCYVLEETSVM | 118. | AEEPTASGGKSTHPM |
| 39. | MYENYIVPEDKREMW | 79. | CCYVLEETSVMLAKR | 119. | TASGGKSTHPMVTRS |
| 40. | YIVPEDKREMWMACI | 80. | LEETSVMLAKRPLIT | 120. | GKSTHPMVTRSKADQ |

Fig. 2

1. MESRGRRCPEMISVL
2. GRRCPEMISVLGPIS
3. PEMISVLGPISGHVL
4. SVLGPISGHVLKAVF
5. PISGHVLKAVFSRGD
6. HVLKAVFSRGDTPVL
7. AVFSRGDTPVLPHET
8. RGDTPVLPHETRLLQ
9. PVLPHETRLLQTGIH
10. HETRLLQTGIHVRVS
11. LLQTGIHVRVSQPSL
12. GIHVRVSQPSLILVS
13. RVSQPSLILVSQYTP
14. PSLILVSQYTPDSTP
15. LVSQYTPDSTPCHRG
16. YTPDSTPCHRGDNQL
17. STPCHRGDNQLQVQH
18. HRGDNQLQVQHTYFT
19. NQLQVQHTYFTGSEV
20. VQHTYFTGSEVENVS
21. YFTGSEVENVSVNVH
22. SEVENVSVNVHNPTG
23. NVSVNVHNPTGRSIC
24. NVHNPTGRSICPSQE
25. PTGRSICPSQEPMSI
26. SICPSQEPMSIYVYA
27. SQEPMSIYVYALPLK
28. MSIYVYALPLKMLNI
29. VYALPLKMLNIPSIN
30. PLKMLNIPSINVHHY
31. LNIPSINVHHYPSAA
32. SINVHHYPSAAERKH
33. HHYPSAAERKHRHLP
34. SAAERKHRHLPVADA
35. RKHRHLPVADAVIHA
36. HLPVADAVIHASGKQ
37. ADAVIHASGKQMWQA
38. IHASGKQMWQARLTV
39. GKQMWQARLTVSGLA
40. WQARLTVSGLAWTRQ
41. LTVSGLAWTRQQNQW
42. GLAWTRQQNQWKEPD
43. TRQQNQWKEPDVYYT
44. NQWKEPDVYYTSAFV
45. EPDVYYTSAFVFPTK
46. YYTSAFVFPTKDVAL
47. AFVFPTKDVALRHVV
48. PTKDVALRHVVCAHE
49. VALRHVVCAHELVCS
50. HVVCAHELVCSMENT
51. AHELVCSMENTRATK
52. VCSMENTRATKMQVI
53. ENTRATKMQVIGDQY

54. ATKMQVIGDQYVKVY
55. QVIGDQYVKVYLESF
56. DQYVKVYLESFCEDV
57. KVYLESFCEDVPSGK
58. ESFCEDVPSGKLFMH
59. EDVPSGKLFMHVTLG
60. SGKLFMHVTLGSDVE
61. FMHVTLGSDVEEDLT
62. TLGSDVEEDLTMTRN
63. DVEEDLTMTRNPQPF
64. DLTMTRNPQPFMRPH
65. TRNPQPFMRPHERNG
66. QPFMRPHERNGFTVL
67. RPHERNGFTVLCPKN
68. RNGFTVLCPKNMIIK
69. TVLCPKNMIIKPGKI
70. PKNMIIKPGKISHIM
71. IIKPGKISHIMLDVA
72. GKISHIMLDVAFTSH
73. HIMLDVAFTSHEHFG
74. DVAFTSHEHFGLLCP
75. TSHEHFGLLCPKSIP
76. HFGLLCPKSIPGLSI
77. LCPKSIPGLSISGNL
78. SIPGLSISGNLLMNG
79. LSISGNLLMNGQQIF
80. GNLLMNGQQIFLEVQ
81. MNGQQIFLEVQAIRE
82. QIFLEVQAIRETVEL
83. EVQAIRETVELRQYD
84. IRETVELRQYDPVAA
85. VELRQYDPVAALFFF
86. QYDPVAALFFFDIDL
87. VAALFFFDIDLLLQR
88. FFFDIDLLLQRGPQY
89. IDLLLQRGPQYSEHP
90. LQRGPQYSEHPTFTS
91. PQYSEHPTFTSQYRI
92. EHPTFTSQYRIQGKL
93. FTSQYRIQGKLEYRH
94. YRIQGKLEYRHTWDR
95. GKLEYRHTWDRHDEG
96. YRHTWDRHDEGAAQG
97. WDRHDEGAAQGDDDV
98. DEGAAQGDDDVWTSG
99. AQGDDDVWTSGSDSD
100. DDVWTSGSDSDEELV
101. TSGSDSDEELVTTER
102. DSDEELVTTERKTPR
103. ELVTTERKTPRVTGG
104. TERKTPRVTGGGAMA
105. TPRVTGGGAMAGAST
106. TGGGAMAGASTSAGR

107. AMAGASTSAGRKRKS
108. ASTSAGRKRKSASSA
109. AGRKRKSASSATACT
110. RKSASSATACTSGVM
111. SSATACTSGVMTRGR
112. ACTSGVMTRGRLKAE
113. GVMTRGRLKAESTVA
114. RGRLKAESTVAPEED
115. KAESTVAPEEDTDED
116. TVAPEEDTDEDSDNE
117. EEDTDEDSDNEIHNP
118. DEDSDNEIHNPAVFT
119. DNEIHNPAVFTWPPW
120. HNPAVFTWPPWQAGI
121. VFTWPPWQAGILARN
122. PPWQAGILARNLVPM
123. AGILARNLVPMVATV
124. ARNLVPMVATVQGQN
125. VPMVATVQGQNLKYQ
126. ATVQGQNLKYQEFFW
127. GQNLKYQEFFWDAND
128. KYQEFFWDANDIYRI
129. FFWDANDIYRIFAEL
130. ANDIYRIFAELEGVW
131. YRIFAELEGVWQPAA
132. AELEGVWQPAAQPKR
133. GVWQPAAQPKRRRHR
134. PAAQPKRRRHRQDAL
135. PKRRRHRQDALPGPC
136. RHRQDALPGPCIAST
137. DALPGPCIASTPKKH
138. LPGPCIASTPKKHRG

SEQUENCE LISTING

<160> NUMBER OF SEQ ID NOS: 260

<210> SEQ ID NO 1
<211> LENGTH: 491
<212> TYPE: PRT
<213> ORGANISM: Artificial Sequence
<220> FEATURE:
<223> OTHER INFORMATION: Description of Artificial Sequence: HCMV IE-1

<400> SEQUENCE: 1

Met Glu Ser Ser Ala Lys Arg Lys Met Asp Pro Asp Asn Pro Asp Glu

-continued

```
            1               5              10              15
Gly Pro Ser Ser Lys Val Pro Arg Pro Glu Thr Pro Val Thr Lys Ala
                20                  25                  30
Thr Thr Phe Leu Gln Thr Met Leu Arg Lys Glu Val Asn Ser Gln Leu
                35                  40                  45
Ser Leu Gly Asp Pro Leu Phe Pro Glu Leu Ala Glu Glu Ser Leu Lys
                50                  55                  60
Thr Phe Glu Gln Val Thr Glu Asp Cys Asn Glu Asn Pro Glu Lys Asp
 65                  70                  75                  80
Val Leu Ala Glu Leu Val Lys Gln Ile Lys Val Arg Val Asp Met Val
                85                  90                  95
Arg His Arg Ile Lys Glu His Met Leu Lys Lys Tyr Thr Gln Thr Glu
                100                 105                 110
Glu Lys Phe Thr Gly Ala Phe Asn Met Met Gly Gly Cys Leu Gln Asn
                115                 120                 125
Ala Leu Asp Ile Leu Asp Lys Val His Glu Pro Phe Glu Glu Met Lys
                130                 135                 140
Cys Ile Gly Leu Thr Met Gln Ser Met Tyr Glu Asn Tyr Ile Val Pro
145                 150                 155                 160
Glu Asp Lys Arg Glu Met Trp Met Ala Cys Ile Lys Glu Leu His Asp
                165                 170                 175
Val Ser Lys Gly Ala Ala Asn Lys Leu Gly Gly Ala Leu Gln Ala Lys
                180                 185                 190
Ala Arg Ala Lys Lys Asp Glu Leu Arg Arg Lys Met Met Tyr Met Cys
                195                 200                 205
Tyr Arg Asn Ile Glu Phe Phe Thr Lys Asn Ser Ala Phe Pro Lys Thr
                210                 215                 220
Thr Asn Gly Cys Ser Gln Ala Met Ala Ala Leu Gln Asn Leu Pro Gln
225                 230                 235                 240
Cys Ser Pro Asp Glu Ile Met Ala Tyr Ala Gln Lys Ile Phe Lys Ile
                245                 250                 255
Leu Asp Glu Glu Arg Asp Lys Val Leu Thr His Ile Asp His Ile Phe
                260                 265                 270
Met Asp Ile Leu Thr Thr Cys Val Glu Thr Met Cys Asn Glu Tyr Lys
                275                 280                 285
Val Thr Ser Asp Ala Cys Met Met Thr Met Tyr Gly Gly Ile Ser Leu
                290                 295                 300
Leu Ser Glu Phe Cys Arg Val Leu Cys Cys Tyr Val Leu Glu Glu Thr
305                 310                 315                 320
Ser Val Met Leu Ala Lys Arg Pro Leu Ile Thr Lys Pro Glu Val Ile
                325                 330                 335
Ser Val Met Lys Arg Arg Ile Glu Glu Ile Cys Met Lys Val Phe Ala
                340                 345                 350
Gln Tyr Ile Leu Gly Ala Asp Pro Leu Arg Val Cys Ser Pro Ser Val
                355                 360                 365
Asp Asp Leu Arg Ala Ile Ala Glu Glu Ser Asp Glu Glu Ala Ile
                370                 375                 380
Val Ala Tyr Thr Leu Ala Thr Ala Gly Val Ser Ser Ser Asp Ser Leu
385                 390                 395                 400
Val Ser Pro Pro Glu Ser Pro Val Pro Ala Thr Ile Pro Leu Ser Ser
                405                 410                 415
Val Ile Val Ala Glu Asn Ser Asp Gln Glu Glu Ser Gln Ser Asp
                420                 425                 430
```

-continued

Glu Glu Glu Glu Glu Gly Ala Gln Glu Glu Arg Glu Asp Thr Val Ser
            435                 440                 445

Val Lys Ser Glu Pro Val Ser Glu Ile Glu Glu Val Ala Pro Glu Glu
        450                 455                 460

Glu Glu Asp Gly Ala Glu Glu Pro Thr Ala Ser Gly Gly Lys Ser Thr
465                 470                 475                 480

His Pro Met Val Thr Arg Ser Lys Ala Asp Gln
                485                 490

<210> SEQ ID NO 2
<211> LENGTH: 561
<212> TYPE: PRT
<213> ORGANISM: Artificial Sequence
<220> FEATURE:
<223> OTHER INFORMATION: Description of Artificial Sequence: HCMV pp65

<400> SEQUENCE: 2

Met Glu Ser Arg Gly Arg Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu

```
                 305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
                340                 345                 350

Ile Asp Leu Leu Leu Gln Arg Gly Pro Gln Tyr Ser Glu His Pro Thr
                355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
                420                 425                 430

Ala Gly Arg Lys Arg Lys Ser Ala Ser Ser Ala Thr Ala Cys Thr Ser
                435                 440                 445

Gly Val Met Thr Arg Gly Arg Leu Lys Ala Glu Ser Thr Val Ala Pro
                450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
                515                 520                 525

Gly Val Trp Gln Pro Ala Ala Gln Pro Lys Arg Arg Arg His Arg Gln
                530                 535                 540

Asp Ala Leu Pro Gly Pro Cys Ile Ala Ser Thr Pro Lys Lys His Arg
545                 550                 555                 560

Gly

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 3

Met Glu Ser Ser Ala Lys Arg Lys Met Asp Pro Asp Asn Pro Asp
  1               5                  10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 4

Gln Thr Met Leu Arg Lys Glu Val Asn Ser Gln Leu Ser Leu Gly
  1               5                  10                  15

<210> SEQ ID NO 5
<211> LENGTH: 15
```

-continued

```
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 5

Ser Asp Ser Leu Val Ser Pro Pro Glu Ser Pro Val Pro Ala Thr
 1               5                  10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 6

Val Ser Pro Pro Glu Ser Pro Val Pro Ala Thr Ile Pro Leu Ser
 1               5                  10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 7

Glu Ser Pro Val Pro Ala Thr Ile Pro Leu Ser Ser Val Ile Val
 1               5                  10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 8

Pro Ala Thr Ile Pro Leu Ser Ser Val Ile Val Ala Glu Asn Ser
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 9

Pro Leu Ser Ser Val Ile Val Ala Glu Asn Ser Asp Gln Glu Glu
 1               5                  10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 10

Val Ile Val Ala Glu Asn Ser Asp Gln Glu Glu Ser Glu Gln Ser
 1               5                  10                  15
```

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 11

Glu Asn Ser Asp Gln Glu Glu Ser Glu Gln Ser Asp Glu Glu Glu
  1               5                  10                  15

<210> SEQ ID NO 12
<211> LENGTH: 15
<212> TYPE: PRT
<213> ORGANISM: Artificial Sequence
<220> FEATURE:
<220> FEATURE:
<223> OTHER INFORMATION: Description of Artificial Sequence: HCMV IE-1
      Fragment

<400> SEQUENCE: 12

Gln Glu Glu Ser Glu Gln Ser Asp Glu Glu Glu Glu Glu Gly Ala
  1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 13

Glu Gln Ser Asp Glu Glu Glu Glu Glu Gly Ala Gln Glu Glu Arg
  1               5                  10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 14

Glu Glu Glu Glu Glu Gly Ala Gln Glu Glu Arg Glu Asp Thr Val
  1               5                  10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 15

Arg Lys Glu Val Asn Ser Gln Leu Ser Leu Gly Asp Pro Leu Phe
  1               5                  10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment -continued

<400> SEQUENCE: 16

Glu Gly Ala Gln Glu Glu Arg Glu Asp Thr Val Ser Val Lys Ser
 1               5                  10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 17

Asn Ser Gln Leu Ser Leu Gly Asp Pro Leu Phe Pro Glu Leu Ala
 1               5                  10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 18

Ser Leu Gly Asp Pro Leu Phe Pro Glu Leu Ala Glu Glu Ser Leu
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 19

Pro Leu Phe Pro Glu Leu Ala Glu Glu Ser Leu Lys Thr Phe Glu
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 20

Glu Leu Ala Glu Glu Ser Leu Lys Thr Phe Glu Gln Val Thr Glu
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 21

Glu Ser Leu Lys Thr Phe Glu Gln Val Thr Glu Asp Cys Asn Glu
 1               5                  10                  15

<210> SEQ ID NO 22
<211> LENGTH: 15
<212> TYPE: PRT

<213> ORGANISM: Artificial Sequence
<220> FEATURE:
<223> OTHER INFORMATION: Description of Artificial Sequence: HCMV IE-1
      Fragment

<400> SEQUENCE: 22

Thr Phe Glu Gln Val Thr Glu Asp Cys Asn Glu Asn Pro Glu Lys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 23

Val Thr Glu Asp Cys Asn Glu Asn Pro Glu Lys Asp Val Leu Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 24

Cys Asn Glu Asn Pro Glu Lys Asp Val Leu Ala Glu Leu Val Lys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 25

Ala Lys Arg Lys Met Asp Pro Asp Asn Pro Asp Glu Gly Pro Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 26

Pro Glu Lys Asp Val Leu Ala Glu Leu Val Lys Gln Ile Lys Val
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 27

Val Leu Ala Glu Leu Val Lys Gln Ile Lys Val Arg Val Asp Met
1               5                   10                  15

```
<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 28

Leu Val Lys Gln Ile Lys Val Arg Val Asp Met Val Arg His Arg
 1               5                  10                  15

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 29

Ile Lys Val Arg Val Asp Met Val Arg His Arg Ile Lys Glu His
 1               5                  10                  15

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 30

Val Asp Met Val Arg His Arg Ile Lys Glu His Met Leu Lys Lys
 1               5                  10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 31

Arg His Arg Ile Lys Glu His Met Leu Lys Lys Tyr Thr Gln Thr
 1               5                  10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 32

Lys Glu His Met Leu Lys Lys Tyr Thr Gln Thr Glu Glu Lys Phe
 1               5                  10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 33
```

Leu Lys Lys Tyr Thr Gln Thr Glu Glu Lys Phe Thr Gly Ala Phe
 1               5                  10                  15

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 34

Thr Gln Thr Glu Glu Lys Phe Thr Gly Ala Phe Asn Met Met Gly
 1               5                  10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 35

Glu Lys Phe Thr Gly Ala Phe Asn Met Met Gly Gly Cys Leu Gln
 1               5                  10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 36

Met Asp Pro Asp Asn Pro Asp Glu Gly Pro Ser Ser Lys Val Pro
 1               5                  10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 37

Gly Ala Phe Asn Met Met Gly Gly Cys Leu Gln Asn Ala Leu Asp
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 38

Met Met Gly Gly Cys Leu Gln Asn Ala Leu Asp Ile Leu Asp Lys
 1               5                  10                  15

<210> SEQ ID NO 39
<211> LENGTH: 15
<212> TYPE: PRT
<213> ORGANISM: Artificial Sequence
<220> FEATURE:

-continued

<223> OTHER INFORMATION: Description of Artificial Sequence: HCMV IE-1
      Fragment

<400> SEQUENCE: 39

Cys Leu Gln Asn Ala Leu Asp Ile Leu Asp Lys Val His Glu Pro
 1               5                  10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 40

Ala Leu Asp Ile Leu Asp Lys Val His Glu Pro Phe Glu Glu Met
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 41

Leu Asp Lys Val His Glu Pro Phe Glu Glu Met Lys Cys Ile Gly
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 42

His Glu Pro Phe Glu Glu Met Lys Cys Ile Gly Leu Thr Met Gln
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 43

Glu Glu Met Lys Cys Ile Gly Leu Thr Met Gln Ser Met Tyr Glu
 1               5                  10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 44

Cys Ile Gly Leu Thr Met Gln Ser Met Tyr Glu Asn Tyr Ile Val
 1               5                  10                  15

<210> SEQ ID NO 45

```
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 45

Thr Met Gln Ser Met Tyr Glu Asn Tyr Ile Val Pro Glu Asp Lys
 1               5                  10                  15

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 46

Met Tyr Glu Asn Tyr Ile Val Pro Glu Asp Lys Arg Glu Met Trp
 1               5                  10                  15

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 47

Asn Pro Asp Glu Gly Pro Ser Ser Lys Val Pro Arg Pro Glu Thr
 1               5                  10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 48

Tyr Ile Val Pro Glu Asp Lys Arg Glu Met Trp Met Ala Cys Ile
 1               5                  10                  15

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 49

Glu Asp Lys Arg Glu Met Trp Met Ala Cys Ile Lys Glu Leu His
 1               5                  10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 50

Glu Met Trp Met Ala Cys Ile Lys Glu Leu His Asp Val Ser Lys
```

<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 51

Ala Cys Ile Lys Glu Leu His Asp Val Ser Lys Gly Ala Ala Asn
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 52

Glu Leu His Asp Val Ser Lys Gly Ala Ala Asn Lys Leu Gly Gly
 1               5                  10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 53

Val Ser Lys Gly Ala Ala Asn Lys Leu Gly Gly Ala Leu Gln Ala
 1               5                  10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 54

Ala Ala Asn Lys Leu Gly Gly Ala Leu Gln Ala Lys Ala Arg Ala
 1               5                  10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 55

Leu Gly Gly Ala Leu Gln Ala Lys Ala Arg Ala Lys Lys Asp Glu
 1               5                  10                  15

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 56

Leu Gln Ala Lys Ala Arg Ala Lys Lys Asp Glu Leu Arg Arg Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 57

Ala Arg Ala Lys Lys Asp Glu Leu Arg Arg Lys Met Met Tyr Met
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 58

Gly Pro Ser Ser Lys Val Pro Arg Pro Glu Thr Pro Val Thr Lys
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 59

Lys Asp Glu Leu Arg Arg Lys Met Met Tyr Met Cys Tyr Arg Asn
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 60

Arg Arg Lys Met Met Tyr Met Cys Tyr Arg Asn Ile Glu Phe Phe
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 61

Met Tyr Met Cys Tyr Arg Asn Ile Glu Phe Phe Thr Lys Asn Ser
1               5                   10                  15

<210> SEQ ID NO 62
<211> LENGTH: 15
<212> TYPE: PRT

```
<213> ORGANISM: Artificial Sequence
<220> FEATURE:
<223> OTHER INFORMATION: Description of Artificial Sequence: HCMV IE-1
      Fragment

<400> SEQUENCE: 62

Tyr Arg Asn Ile Glu Phe Phe Thr Lys Asn Ser Ala Phe Pro Lys
 1               5                  10                  15

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 63

Glu Phe Phe Thr Lys Asn Ser Ala Phe Pro Lys Thr Thr Asn Gly
 1               5                  10                  15

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 64

Lys Asn Ser Ala Phe Pro Lys Thr Thr Asn Gly Cys Ser Gln Ala
 1               5                  10                  15

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 65

Phe Pro Lys Thr Thr Asn Gly Cys Ser Gln Ala Met Ala Ala Leu
 1               5                  10                  15

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 66

Thr Asn Gly Cys Ser Gln Ala Met Ala Ala Leu Gln Asn Leu Pro
 1               5                  10                  15

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 67

Ser Gln Ala Met Ala Ala Leu Gln Asn Leu Pro Gln Cys Ser Pro
 1               5                  10                  15
```

```
<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 68

Ala Ala Leu Gln Asn Leu Pro Gln Cys Ser Pro Asp Glu Ile Met
 1               5                  10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 69

Lys Val Pro Arg Pro Glu Thr Pro Val Thr Lys Ala Thr Thr Phe
 1               5                  10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 70

Asn Leu Pro Gln Cys Ser Pro Asp Glu Ile Met Ala Tyr Ala Gln
 1               5                  10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 71

Cys Ser Pro Asp Glu Ile Met Ala Tyr Ala Gln Lys Ile Phe Lys
 1               5                  10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 72

Glu Ile Met Ala Tyr Ala Gln Lys Ile Phe Lys Ile Leu Asp Glu
 1               5                  10                  15

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 73
```

```
<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 74

Ile Phe Lys Ile Leu Asp Glu Glu Arg Asp Lys Val Leu Thr His
 1               5                  10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 75

Leu Asp Glu Glu Arg Asp Lys Val Leu Thr His Ile Asp His Ile
 1               5                  10                  15

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 76

Arg Asp Lys Val Leu Thr His Ile Asp His Ile Phe Met Asp Ile
 1               5                  10                  15

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 77

Leu Thr His Ile Asp His Ile Phe Met Asp Ile Leu Thr Thr Cys
 1               5                  10                  15

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 78

Asp His Ile Phe Met Asp Ile Leu Thr Thr Cys Val Glu Thr Met
 1               5                  10                  15

<210> SEQ ID NO 79
<211> LENGTH: 15
<212> TYPE: PRT
<213> ORGANISM: Artificial Sequence
<220> FEATURE:
```

-continued

<223> OTHER INFORMATION: Description of Artificial Sequence: HCMV IE-1
      Fragment

<400> SEQUENCE: 79

Met Asp Ile Leu Thr Thr Cys Val Glu Thr Met Cys Asn Glu Tyr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 80

Pro Glu Thr Pro Val Thr Lys Ala Thr Thr Phe Leu Gln Thr Met
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 81

Thr Thr Cys Val Glu Thr Met Cys Asn Glu Tyr Lys Val Thr Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 82

Glu Thr Met Cys Asn Glu Tyr Lys Val Thr Ser Asp Ala Cys Met
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 83

Asn Glu Tyr Lys Val Thr Ser Asp Ala Cys Met Met Thr Met Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 84

Val Thr Ser Asp Ala Cys Met Met Thr Met Tyr Gly Gly Ile Ser
1               5                   10                  15

<210> SEQ ID NO 85

-continued

```
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 85

Ala Cys Met Met Thr Met Tyr Gly Gly Ile Ser Leu Leu Ser Glu
 1               5                  10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 86

Thr Met Tyr Gly Gly Ile Ser Leu Leu Ser Glu Phe Cys Arg Val
 1               5                  10                  15

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 87

Gly Ile Ser Leu Leu Ser Glu Phe Cys Arg Val Leu Cys Cys Tyr
 1               5                  10                  15

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 88

Leu Ser Glu Phe Cys Arg Val Leu Cys Cys Tyr Val Leu Glu Glu
 1               5                  10                  15

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 89

Cys Arg Val Leu Cys Cys Tyr Val Leu Glu Glu Thr Ser Val Met
 1               5                  10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 90

Cys Cys Tyr Val Leu Glu Glu Thr Ser Val Met Leu Ala Lys Arg
```

-continued

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment

<400> SEQUENCE: 91

Val Thr Lys Ala Thr Thr Phe Leu Gln Thr Met Leu Arg Lys Glu
 1               5                  10                  15

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment

<400> SEQUENCE: 92

Leu Glu Glu Thr Ser Val Met Leu Ala Lys Arg Pro Leu Ile Thr
 1               5                  10                  15

<210> SEQ ID NO 93
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment

<400> SEQUENCE: 93

Ser Val Met Leu Ala Lys Arg Pro Leu Ile Thr Lys Pro Glu Val
 1               5                  10                  15

<210> SEQ ID NO 94
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment

<400> SEQUENCE: 94

Ala Lys Arg Pro Leu Ile Thr Lys Pro Glu Val Ile Ser Val Met
 1               5                  10                  15

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment

<400> SEQUENCE: 95

Leu Ile Thr Lys Pro Glu Val Ile Ser Val Met Lys Arg Arg Ile
 1               5                  10                  15

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: HCMV IE-1
    Fragment -continued

<400> SEQUENCE: 96

Pro Glu Val Ile Ser Val Met Lys Arg Arg Ile Glu Glu Ile Cys
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 97

Ser Val Met Lys Arg Arg Ile Glu Glu Ile Cys Met Lys Val Phe
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 98

Arg Arg Ile Glu Glu Ile Cys Met Lys Val Phe Ala Gln Tyr Ile
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 99

Glu Ile Cys Met Lys Val Phe Ala Gln Tyr Ile Leu Gly Ala Asp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 100

Lys Val Phe Ala Gln Tyr Ile Leu Gly Ala Asp Pro Leu Arg Val
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 101

Gln Tyr Ile Leu Gly Ala Asp Pro Leu Arg Val Cys Ser Pro Ser
1               5                   10                  15

<210> SEQ ID NO 102
<211> LENGTH: 15
<212> TYPE: PRT

```
<213> ORGANISM: Artificial Sequence
<220> FEATURE:
<223> OTHER INFORMATION: Description of Artificial Sequence: HCMV IE-1
      Fragment

<400> SEQUENCE: 102

Thr Thr Phe Leu Gln Thr Met Leu Arg Lys Glu Val Asn Ser Gln
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 103

Gly Ala Asp Pro Leu Arg Val Cys Ser Pro Ser Val Asp Asp Leu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 104

Leu Arg Val Cys Ser Pro Ser Val Asp Asp Leu Arg Ala Ile Ala
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 105

Ser Pro Ser Val Asp Asp Leu Arg Ala Ile Ala Glu Glu Ser Asp
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 106

Asp Asp Leu Arg Ala Ile Ala Glu Glu Ser Asp Glu Glu Glu Ala
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 107

Ala Ile Ala Glu Glu Ser Asp Glu Glu Glu Ala Ile Val Ala Tyr
1               5                   10                  15
```

```
<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 108

Glu Ser Asp Glu Glu Glu Ala Ile Val Ala Tyr Thr Leu Ala Thr
  1               5                  10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 109

Glu Glu Ala Ile Val Ala Tyr Thr Leu Ala Thr Ala Gly Val Ser
  1               5                  10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 110

Val Ala Tyr Thr Leu Ala Thr Ala Gly Val Ser Ser Ser Asp Ser
  1               5                  10                  15

<210> SEQ ID NO 111
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 111

Leu Ala Thr Ala Gly Val Ser Ser Ser Asp Ser Leu Val Ser Pro
  1               5                  10                  15

<210> SEQ ID NO 112
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 112

Gly Val Ser Ser Ser Asp Ser Leu Val Ser Pro Pro Glu Ser Pro
  1               5                  10                  15

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 113
```

```
Glu Glu Arg Glu Asp Thr Val Ser Val Lys Ser Glu Pro Val Ser
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 114

Asp Thr Val Ser Val Lys Ser Glu Pro Val Ser Glu Ile Glu Glu
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 115

Val Lys Ser Glu Pro Val Ser Glu Ile Glu Glu Val Ala Pro Glu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 116

Pro Val Ser Glu Ile Glu Glu Val Ala Pro Glu Glu Glu Glu Asp
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 117

Ile Glu Glu Val Ala Pro Glu Glu Glu Glu Asp Gly Ala Glu Glu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 118

Ala Pro Glu Glu Glu Glu Asp Gly Ala Glu Glu Pro Thr Ala Ser
1               5                   10                  15

<210> SEQ ID NO 119
<211> LENGTH: 15
<212> TYPE: PRT
<213> ORGANISM: Artificial Sequence
<220> FEATURE:
```

-continued

<223> OTHER INFORMATION: Description of Artificial Sequence: HCMV IE-1
      Fragment

<400> SEQUENCE: 119

Glu Glu Asp Gly Ala Glu Glu Pro Thr Ala Ser Gly Gly Lys Ser
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 120

Ala Glu Glu Pro Thr Ala Ser Gly Gly Lys Ser Thr His Pro Met
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 121

Thr Ala Ser Gly Gly Lys Ser Thr His Pro Met Val Thr Arg Ser
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: HCMV IE-1
      Fragment

<400> SEQUENCE: 122

Gly Lys Ser Thr His Pro Met Val Thr Arg Ser Lys Ala Asp Gln
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 123

Met Glu Ser Arg Gly Arg Arg Cys Pro Glu Met Ile Ser Val Leu
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 124

His Glu Thr Arg Leu Leu Gln Thr Gly Ile His Val Arg Val Ser
1               5                   10                  15

<210> SEQ ID NO 125

```
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 125

Asp Asp Val Trp Thr Ser Gly Ser Asp Ser Asp Glu Glu Leu Val
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 126

Thr Ser Gly Ser Asp Ser Asp Glu Glu Leu Val Thr Thr Glu Arg
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 127

Asp Ser Asp Glu Glu Leu Val Thr Thr Glu Arg Lys Thr Pro Arg
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 128

Glu Leu Val Thr Thr Glu Arg Lys Thr Pro Arg Val Thr Gly Gly
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 129

Thr Glu Arg Lys Thr Pro Arg Val Thr Gly Gly Gly Ala Met Ala
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 130

Thr Pro Arg Val Thr Gly Gly Gly Ala Met Ala Gly Ala Ser Thr
```

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 131

Thr Gly Gly Gly Ala Met Ala Gly Ala Ser Thr Ser Ala Gly Arg
 1               5                  10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 132

Ala Met Ala Gly Ala Ser Thr Ser Ala Gly Arg Lys Arg Lys Ser
 1               5                  10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 133

Ala Ser Thr Ser Ala Gly Arg Lys Arg Lys Ser Ala Ser Ser Ala
 1               5                  10                  15

<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 134

Ala Gly Arg Lys Arg Lys Ser Ala Ser Ser Ala Thr Ala Cys Thr
 1               5                  10                  15

<210> SEQ ID NO 135
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 135

Leu Leu Gln Thr Gly Ile His Val Arg Val Ser Gln Pro Ser Leu
 1               5                  10                  15

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

```
<400> SEQUENCE: 136

Arg Lys Ser Ala Ser Ser Ala Thr Ala Cys Thr Ser Gly Val Met
  1               5                  10                  15

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 137

Ser Ser Ala Thr Ala Cys Thr Ser Gly Val Met Thr Arg Gly Arg
  1               5                  10                  15

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 138

Gly Ile His Val Arg Val Ser Gln Pro Ser Leu Ile Leu Val Ser
  1               5                  10                  15

<210> SEQ ID NO 139
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 139

Arg Val Ser Gln Pro Ser Leu Ile Leu Val Ser Gln Tyr Thr Pro
  1               5                  10                  15

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 140

Pro Ser Leu Ile Leu Val Ser Gln Tyr Thr Pro Asp Ser Thr Pro
  1               5                  10                  15

<210> SEQ ID NO 141
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 141

Leu Val Ser Gln Tyr Thr Pro Asp Ser Thr Pro Cys His Arg Gly
  1               5                  10                  15

<210> SEQ ID NO 142
<211> LENGTH: 15
<212> TYPE: PRT
```

```
<213> ORGANISM: Artificial Sequence
<220> FEATURE:
<223> OTHER INFORMATION: Description of Artificial Sequence: HCMV pp65
      Fragment

<400> SEQUENCE: 142

Tyr Thr Pro Asp Ser Thr Pro Cys His Arg Gly Asp Asn Gln Leu
 1               5                  10                  15

<210> SEQ ID NO 143
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 143

Ser Thr Pro Cys His Arg Gly Asp Asn Gln Leu Gln Val Gln His
 1               5                  10                  15

<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 144

His Arg Gly Asp Asn Gln Leu Gln Val Gln His Thr Tyr Phe Thr
 1               5                  10                  15

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 145

Asn Gln Leu Gln Val Gln His Thr Tyr Phe Thr Gly Ser Glu Val
 1               5                  10                  15

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 146

Gly Arg Arg Cys Pro Glu Met Ile Ser Val Leu Gly Pro Ile Ser
 1               5                  10                  15

<210> SEQ ID NO 147
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 147

Val Gln His Thr Tyr Phe Thr Gly Ser Glu Val Glu Asn Val Ser
 1               5                  10                  15
```

```
<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 148

Tyr Phe Thr Gly Ser Glu Val Glu Asn Val Ser Val Asn Val His
 1               5                  10                  15

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 149

Ser Glu Val Glu Asn Val Ser Val Asn Val His Asn Pro Thr Gly
 1               5                  10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 150

Asn Val Ser Val Asn Val His Asn Pro Thr Gly Arg Ser Ile Cys
 1               5                  10                  15

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 151

Asn Val His Asn Pro Thr Gly Arg Ser Ile Cys Pro Ser Gln Glu
 1               5                  10                  15

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 152

Pro Thr Gly Arg Ser Ile Cys Pro Ser Gln Glu Pro Met Ser Ile
 1               5                  10                  15

<210> SEQ ID NO 153
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 153
```

```
Ser Ile Cys Pro Ser Gln Glu Pro Met Ser Ile Tyr Val Tyr Ala
 1               5                  10                  15

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 154

Ser Gln Glu Pro Met Ser Ile Tyr Val Tyr Ala Leu Pro Leu Lys
 1               5                  10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 155

Met Ser Ile Tyr Val Tyr Ala Leu Pro Leu Lys Met Leu Asn Ile
 1               5                  10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 156

Val Tyr Ala Leu Pro Leu Lys Met Leu Asn Ile Pro Ser Ile Asn
 1               5                  10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 157

Pro Glu Met Ile Ser Val Leu Gly Pro Ile Ser Gly His Val Leu
 1               5                  10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 158

Pro Leu Lys Met Leu Asn Ile Pro Ser Ile Asn Val His His Tyr
 1               5                  10                  15

<210> SEQ ID NO 159
<211> LENGTH: 15
<212> TYPE: PRT
<213> ORGANISM: Artificial Sequence
<220> FEATURE:
```

-continued

<223> OTHER INFORMATION: Description of Artificial Sequence: HCMV pp65
      Fragment

<400> SEQUENCE: 159

Leu Asn Ile Pro Ser Ile Asn Val His His Tyr Pro Ser Ala Ala
 1               5                  10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 160

Ser Ile Asn Val His His Tyr Pro Ser Ala Ala Glu Arg Lys His
 1               5                  10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 161

His His Tyr Pro Ser Ala Ala Glu Arg Lys His Arg His Leu Pro
 1               5                  10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 162

Ser Ala Ala Glu Arg Lys His Arg His Leu Pro Val Ala Asp Ala
 1               5                  10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 163

Arg Lys His Arg His Leu Pro Val Ala Asp Ala Val Ile His Ala
 1               5                  10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 164

His Leu Pro Val Ala Asp Ala Val Ile His Ala Ser Gly Lys Gln
 1               5                  10                  15

<210> SEQ ID NO 165

```
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 165

Ala Asp Ala Val Ile His Ala Ser Gly Lys Gln Met Trp Gln Ala
 1               5                  10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 166

Ile His Ala Ser Gly Lys Gln Met Trp Gln Ala Arg Leu Thr Val
 1               5                  10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 167

Gly Lys Gln Met Trp Gln Ala Arg Leu Thr Val Ser Gly Leu Ala
 1               5                  10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 168

Ser Val Leu Gly Pro Ile Ser Gly His Val Leu Lys Ala Val Phe
 1               5                  10                  15

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 169

Trp Gln Ala Arg Leu Thr Val Ser Gly Leu Ala Trp Thr Arg Gln
 1               5                  10                  15

<210> SEQ ID NO 170
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 170

Leu Thr Val Ser Gly Leu Ala Trp Thr Arg Gln Gln Asn Gln Trp
```

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 171

Gly Leu Ala Trp Thr Arg Gln Gln Asn Gln Trp Lys Glu Pro Asp
 1               5                  10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 172

Thr Arg Gln Gln Asn Gln Trp Lys Glu Pro Asp Val Tyr Tyr Thr
 1               5                  10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 173

Asn Gln Trp Lys Glu Pro Asp Val Tyr Tyr Thr Ser Ala Phe Val
 1               5                  10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 174

Glu Pro Asp Val Tyr Tyr Thr Ser Ala Phe Val Phe Pro Thr Lys
 1               5                  10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 175

Tyr Tyr Thr Ser Ala Phe Val Phe Pro Thr Lys Asp Val Ala Leu
 1               5                  10                  15

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment -continued

```
<400> SEQUENCE: 176

Ala Phe Val Phe Pro Thr Lys Asp Val Ala Leu Arg His Val Val
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 177

Pro Thr Lys Asp Val Ala Leu Arg His Val Val Cys Ala His Glu
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 178

Val Ala Leu Arg His Val Val Cys Ala His Glu Leu Val Cys Ser
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 179

Pro Ile Ser Gly His Val Leu Lys Ala Val Phe Ser Arg Gly Asp
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 180

His Val Val Cys Ala His Glu Leu Val Cys Ser Met Glu Asn Thr
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 181

Ala His Glu Leu Val Cys Ser Met Glu Asn Thr Arg Ala Thr Lys
1               5                   10                  15

<210> SEQ ID NO 182
<211> LENGTH: 15
<212> TYPE: PRT
```

```
<213> ORGANISM: Artificial Sequence
<220> FEATURE:
<223> OTHER INFORMATION: Description of Artificial Sequence: HCMV pp65
      Fragment

<400> SEQUENCE: 182

Val Cys Ser Met Glu Asn Thr Arg Ala Thr Lys Met Gln Val Ile
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 183

Glu Asn Thr Arg Ala Thr Lys Met Gln Val Ile Gly Asp Gln Tyr
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 184

Ala Thr Lys Met Gln Val Ile Gly Asp Gln Tyr Val Lys Val Tyr
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 185

Gln Val Ile Gly Asp Gln Tyr Val Lys Val Tyr Leu Glu Ser Phe
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 186

Asp Gln Tyr Val Lys Val Tyr Leu Glu Ser Phe Cys Glu Asp Val
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 187

Lys Val Tyr Leu Glu Ser Phe Cys Glu Asp Val Pro Ser Gly Lys
1               5                   10                  15
```

-continued

<210> SEQ ID NO 188
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 188

Glu Ser Phe Cys Glu Asp Val Pro Ser Gly Lys Leu Phe Met His
 1               5                  10                  15

<210> SEQ ID NO 189
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 189

Glu Asp Val Pro Ser Gly Lys Leu Phe Met His Val Thr Leu Gly
 1               5                  10                  15

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 190

His Val Leu Lys Ala Val Phe Ser Arg Gly Asp Thr Pro Val Leu
 1               5                  10                  15

<210> SEQ ID NO 191
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 191

Ser Gly Lys Leu Phe Met His Val Thr Leu Gly Ser Asp Val Glu
 1               5                  10                  15

<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 192

Phe Met His Val Thr Leu Gly Ser Asp Val Glu Glu Asp Leu Thr
 1               5                  10                  15

<210> SEQ ID NO 193
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 193

```
Thr Leu Gly Ser Asp Val Glu Glu Asp Leu Thr Met Thr Arg Asn
 1               5                  10                  15

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 194

Asp Val Glu Glu Asp Leu Thr Met Thr Arg Asn Pro Gln Pro Phe
 1               5                  10                  15

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 195

Asp Leu Thr Met Thr Arg Asn Pro Gln Pro Phe Met Arg Pro His
 1               5                  10                  15

<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 196

Thr Arg Asn Pro Gln Pro Phe Met Arg Pro His Glu Arg Asn Gly
 1               5                  10                  15

<210> SEQ ID NO 197
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 197

Gln Pro Phe Met Arg Pro His Glu Arg Asn Gly Phe Thr Val Leu
 1               5                  10                  15

<210> SEQ ID NO 198
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 198

Arg Pro His Glu Arg Asn Gly Phe Thr Val Leu Cys Pro Lys Asn
 1               5                  10                  15

<210> SEQ ID NO 199
<211> LENGTH: 15
<212> TYPE: PRT
<213> ORGANISM: Artificial Sequence
<220> FEATURE:
```

<223> OTHER INFORMATION: Description of Artificial Sequence: HCMV pp65
      Fragment

<400> SEQUENCE: 199

Arg Asn Gly Phe Thr Val Leu Cys Pro Lys Asn Met Ile Ile Lys
 1               5                  10                  15

<210> SEQ ID NO 200
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 200

Thr Val Leu Cys Pro Lys Asn Met Ile Ile Lys Pro Gly Lys Ile
 1               5                  10                  15

<210> SEQ ID NO 201
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 201

Ala Val Phe Ser Arg Gly Asp Thr Pro Val Leu Pro His Glu Thr
 1               5                  10                  15

<210> SEQ ID NO 202
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 202

Pro Lys Asn Met Ile Ile Lys Pro Gly Lys Ile Ser His Ile Met
 1               5                  10                  15

<210> SEQ ID NO 203
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 203

Ile Ile Lys Pro Gly Lys Ile Ser His Ile Met Leu Asp Val Ala
 1               5                  10                  15

<210> SEQ ID NO 204
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 204

Gly Lys Ile Ser His Ile Met Leu Asp Val Ala Phe Thr Ser His
 1               5                  10                  15

<210> SEQ ID NO 205

```
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 205

His Ile Met Leu Asp Val Ala Phe Thr Ser His Glu His Phe Gly
 1               5                  10                  15

<210> SEQ ID NO 206
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 206

Asp Val Ala Phe Thr Ser His Glu His Phe Gly Leu Leu Cys Pro
 1               5                  10                  15

<210> SEQ ID NO 207
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 207

Thr Ser His Glu His Phe Gly Leu Leu Cys Pro Lys Ser Ile Pro
 1               5                  10                  15

<210> SEQ ID NO 208
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 208

His Phe Gly Leu Leu Cys Pro Lys Ser Ile Pro Gly Leu Ser Ile
 1               5                  10                  15

<210> SEQ ID NO 209
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 209

Leu Cys Pro Lys Ser Ile Pro Gly Leu Ser Ile Ser Gly Asn Leu
 1               5                  10                  15

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 210

Ser Ile Pro Gly Leu Ser Ile Ser Gly Asn Leu Leu Met Asn Gly
```

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 211

Leu Ser Ile Ser Gly Asn Leu Leu Met Asn Gly Gln Gln Ile Phe
 1               5                  10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 212

Arg Gly Asp Thr Pro Val Leu Pro His Glu Thr Arg Leu Leu Gln
 1               5                  10                  15

<210> SEQ ID NO 213
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 213

Gly Asn Leu Leu Met Asn Gly Gln Gln Ile Phe Leu Glu Val Gln
 1               5                  10                  15

<210> SEQ ID NO 214
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 214

Met Asn Gly Gln Gln Ile Phe Leu Glu Val Gln Ala Ile Arg Glu
 1               5                  10                  15

<210> SEQ ID NO 215
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

<400> SEQUENCE: 215

Gln Ile Phe Leu Glu Val Gln Ala Ile Arg Glu Thr Val Glu Leu
 1               5                  10                  15

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: HCMV pp65
    Fragment

```
<400> SEQUENCE: 216

Glu Val Gln Ala Ile Arg Glu Thr Val Glu Leu Arg Gln Tyr Asp
 1               5                  10                  15

<210> SEQ ID NO 217
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 217

Ile Arg Glu Thr Val Glu Leu Arg Gln Tyr Asp Pro Val Ala Ala
 1               5                  10                  15

<210> SEQ ID NO 218
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 218

Val Glu Leu Arg Gln Tyr Asp Pro Val Ala Ala Leu Phe Phe Phe
 1               5                  10                  15

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 219

Gln Tyr Asp Pro Val Ala Ala Leu Phe Phe Phe Asp Ile Asp Leu
 1               5                  10                  15

<210> SEQ ID NO 220
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 220

Val Ala Ala Leu Phe Phe Phe Asp Ile Asp Leu Leu Leu Gln Arg
 1               5                  10                  15

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 221

Phe Phe Phe Asp Ile Asp Leu Leu Leu Gln Arg Gly Pro Gln Tyr
 1               5                  10                  15

<210> SEQ ID NO 222
<211> LENGTH: 15
<212> TYPE: PRT
```

-continued

```
<213> ORGANISM: Artificial Sequence
<220> FEATURE:
<223> OTHER INFORMATION: Description of Artificial Sequence: HCMV pp65
      Fragment

<400> SEQUENCE: 222

Ile Asp Leu Leu Leu Gln Arg Gly Pro Gln Tyr Ser Glu His Pro
 1               5                  10                  15

<210> SEQ ID NO 223
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 223

Pro Val Leu Pro His Glu Thr Arg Leu Leu Gln Thr Gly Ile His
 1               5                  10                  15

<210> SEQ ID NO 224
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 224

Leu Gln Arg Gly Pro Gln Tyr Ser Glu His Pro Thr Phe Thr Ser
 1               5                  10                  15

<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 225

Pro Gln Tyr Ser Glu His Pro Thr Phe Thr Ser Gln Tyr Arg Ile
 1               5                  10                  15

<210> SEQ ID NO 226
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 226

Glu His Pro Thr Phe Thr Ser Gln Tyr Arg Ile Gln Gly Lys Leu
 1               5                  10                  15

<210> SEQ ID NO 227
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 227

Phe Thr Ser Gln Tyr Arg Ile Gln Gly Lys Leu Glu Tyr Arg His
 1               5                  10                  15
```

-continued

<210> SEQ ID NO 228
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 228

Tyr Arg Ile Gln Gly Lys Leu Glu Tyr Arg His Thr Trp Asp Arg
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 229

Gly Lys Leu Glu Tyr Arg His Thr Trp Asp Arg His Asp Glu Gly
1               5                   10                  15

<210> SEQ ID NO 230
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 230

Tyr Arg His Thr Trp Asp Arg His Asp Glu Gly Ala Ala Gln Gly
1               5                   10                  15

<210> SEQ ID NO 231
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 231

Trp Asp Arg His Asp Glu Gly Ala Ala Gln Gly Asp Asp Asp Val
1               5                   10                  15

<210> SEQ ID NO 232
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 232

Asp Glu Gly Ala Ala Gln Gly Asp Asp Asp Val Trp Thr Ser Gly
1               5                   10                  15

<210> SEQ ID NO 233
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 233

```
Ala Gln Gly Asp Asp Val Trp Thr Ser Gly Ser Asp Ser Asp
 1               5                  10                 15

<210> SEQ ID NO 234
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 234

Ala Cys Thr Ser Gly Val Met Thr Arg Gly Arg Leu Lys Ala Glu
 1               5                  10                 15

<210> SEQ ID NO 235
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 235

Gly Val Met Thr Arg Gly Arg Leu Lys Ala Glu Ser Thr Val Ala
 1               5                  10                 15

<210> SEQ ID NO 236
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 236

Arg Gly Arg Leu Lys Ala Glu Ser Thr Val Ala Pro Glu Glu Asp
 1               5                  10                 15

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 237

Lys Ala Glu Ser Thr Val Ala Pro Glu Glu Asp Thr Asp Glu Asp
 1               5                  10                 15

<210> SEQ ID NO 238
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 238

Thr Val Ala Pro Glu Glu Asp Thr Asp Glu Asp Ser Asp Asn Glu
 1               5                  10                 15

<210> SEQ ID NO 239
<211> LENGTH: 15
<212> TYPE: PRT
<213> ORGANISM: Artificial Sequence
<220> FEATURE:
```

-continued

<223> OTHER INFORMATION: Description of Artificial Sequence: HCMV pp65
      Fragment

<400> SEQUENCE: 239

Glu Glu Asp Thr Asp Glu Asp Ser Asp Asn Glu Ile His Asn Pro
1               5                   10                  15

<210> SEQ ID NO 240
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 240

Asp Glu Asp Ser Asp Asn Glu Ile His Asn Pro Ala Val Phe Thr
1               5                   10                  15

<210> SEQ ID NO 241
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 241

Asp Asn Glu Ile His Asn Pro Ala Val Phe Thr Trp Pro Pro Trp
1               5                   10                  15

<210> SEQ ID NO 242
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 242

His Asn Pro Ala Val Phe Thr Trp Pro Pro Trp Gln Ala Gly Ile
1               5                   10                  15

<210> SEQ ID NO 243
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 243

Val Phe Thr Trp Pro Pro Trp Gln Ala Gly Ile Leu Ala Arg Asn
1               5                   10                  15

<210> SEQ ID NO 244
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 244

Pro Pro Trp Gln Ala Gly Ile Leu Ala Arg Asn Leu Val Pro Met
1               5                   10                  15

<210> SEQ ID NO 245

```
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 245

Ala Gly Ile Leu Ala Arg Asn Leu Val Pro Met Val Ala Thr Val
 1               5                  10                  15

<210> SEQ ID NO 246
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 246

Ala Arg Asn Leu Val Pro Met Val Ala Thr Val Gln Gly Gln Asn
 1               5                  10                  15

<210> SEQ ID NO 247
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 247

Val Pro Met Val Ala Thr Val Gln Gly Gln Asn Leu Lys Tyr Gln
 1               5                  10                  15

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 248

Ala Thr Val Gln Gly Gln Asn Leu Lys Tyr Gln Glu Phe Phe Trp
 1               5                  10                  15

<210> SEQ ID NO 249
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 249

Gly Gln Asn Leu Lys Tyr Gln Glu Phe Phe Trp Asp Ala Asn Asp
 1               5                  10                  15

<210> SEQ ID NO 250
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 250

Lys Tyr Gln Glu Phe Phe Trp Asp Ala Asn Asp Ile Tyr Arg Ile
```

-continued

<210> SEQ ID NO 251
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 251

Phe Phe Trp Asp Ala Asn Asp Ile Tyr Arg Ile Phe Ala Glu Leu
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 252

Ala Asn Asp Ile Tyr Arg Ile Phe Ala Glu Leu Glu Gly Val Trp
1               5                   10                  15

<210> SEQ ID NO 253
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 253

Tyr Arg Ile Phe Ala Glu Leu Glu Gly Val Trp Gln Pro Ala Ala
1               5                   10                  15

<210> SEQ ID NO 254
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 254

Ala Glu Leu Glu Gly Val Trp Gln Pro Ala Ala Gln Pro Lys Arg
1               5                   10                  15

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 255

Gly Val Trp Gln Pro Ala Ala Gln Pro Lys Arg Arg Arg His Arg
1               5                   10                  15

<210> SEQ ID NO 256
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

```
<400> SEQUENCE: 256

Pro Ala Ala Gln Pro Lys Arg Arg Arg His Arg Gln Asp Ala Leu
1               5                   10                  15

<210> SEQ ID NO 257
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 257

Pro Lys Arg Arg Arg His Arg Gln Asp Ala Leu Pro Gly Pro Cys
1               5                   10                  15

<210> SEQ ID NO 258
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 258

Arg His Arg Gln Asp Ala Leu Pro Gly Pro Cys Ile Ala Ser Thr
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 259

Asp Ala Leu Pro Gly Pro Cys Ile Ala Ser Thr Pro Lys Lys His
1               5                   10                  15

<210> SEQ ID NO 260
<211> LENGTH: 15
<212> TYPE: PRT
<213> ORGANISM: Artificial Sequence
<220> FEATURE:
<223> OTHER INFORMATION: Description of Artificial Sequence: HCMV pp65
      Fragment

<400> SEQUENCE: 260

Leu Pro Gly Pro Cys Ile Ala Ser Thr Pro Lys Lys His Arg Gly
1               5                   10                  15
```

METHOD FOR ANTIGEN-SPECIFIC STIMULATION OF T LYMPHOCYTES WITH SYNTHETIC PEPTIDE LIBRARIES

This application is a 371 of PCT/EP01/01773, filed Feb. 17, 2001.

The invention relates to a method for antigen-specific stimulation of T lymphocytes with synthetic peptide libraries, comprising the following steps:
(a) subdividing the total amino acid sequence of the antigen into protein fragments with partial amino acid sequences;
(b) synthesizing a peptide library containing these protein fragments;
(c) incubating a suspension containing CD8+ and/or CD4+ T lymphocytes with all the protein fragments of the peptide library in a single culture run.

The method can be employed for both the immunostimulation of T lymphocytes of mammals, especially humans, and for diagnostics in order to establish whether a mammal, especially a human, has previously responded to a specific protein with its immune system, and if so, how strong such response is.

BACKGROUND OF THE INVENTION

The immune response of CD8+ T lymphocytes to protein antigens can be detected only with a great expenditure using known methods. It depends on the presentation of the epitopes derived from these antigens on MHC class I molecules on cells and can be measured through measuring a cytotoxic response induced by exposure. This experimental set-up is usual and takes one to several weeks in which the CD8+ T lymphocytes must be stimulated with the antigen in a suitable cell culture and are then incubated in a cytotoxicity test with suitable target cells which have been loaded with peptides from this antigen or transfected with the antigen or parts thereof. The induction of a response of the CD8+ T lymphocytes is measured from the degree of destruction of target cells, which requires suitable controls and includes a great experimental and time expenditure.

The detection of the immune response of CD4+ T lymphocytes to protein antigens is somewhat less complicated. The response of CD4+ T lymphocytes to protein antigens depends on the presentation of the epitopes derived from these antigens on MHC class II molecules on cells and can be measured through the proliferation of such cells in the presence of the antigen or upon exposure to this antigen, e.g., through the incorporation of tritiated thymidine. This experimental set-up is usual and takes several days up to a week or longer. The presence of a CD4+ T lymphocyte response to protein antigens can further be measured in a known method in which a suspension containing CD4+ T lymphocytes is incubated with the corresponding protein followed by detecting the CD4+ T lymphocyte induction through the presence of intracellular cytokines by flow cytometry.

The presence of a CD8+ T lymphocyte or CD4+ T lymphocyte response to individual epitopes can further be measured in a known method in which a suspension containing CD8+ and/or CD4+ T lymphocytes is incubated with peptides from this protein followed by detecting the CD8+ or CD4+ T lymphocyte induction through the presence of intracellular cytokines by flow cytometry, making use of the fact that peptides can be charged directly from outside onto the MHC class I or MHC class II molecules on cells, circumventing intracellular processing. In this method, it can be achieved by a suitable grouping of peptides that stimulating peptides can be identified and thus epitopes can be determined. The grouping used in this way distributes all possible epitopes to several, and mostly a large number of, runs so that it can be established whether individual peptides from this protein can induce a T lymphocyte response and it can be established which of the peptides occurring in the individual groups have led to such stimulation (this is described in F. Kern et al., Journal of Virology, October 1999, p. 8179-8184, and in WO 99/36568).

However, this grouping allows neither to determine systematically in a single measurement with a corresponding control whether a T lymphocyte response against the protein is present at all, nor to tell how strong the response (the proportion of the reactive lymphocytes in percent of the total CD8+ or CD4+ T lymphocytes) to this protein is all in all. To do this, the usual grouping in this method for the identification of epitopes would require several stimulation and measuring runs, depending on the number of peptides used. The application described in the literature aims at the precise identification of epitopes and therefore uses groups of peptides whose size is chosen in such a way that as few as possible individual peptides must be tested to establish the stimulating activity of a peptide group. However, the smaller the group size is chosen, the more groups have to be tested. Therefore, as the most favorable variant, a number of groups is chosen in this method which is twice the square root of the next square number exceeding the number of the peptides (unless the number of peptides is itself a square number).

This may be exemplified by the pp65 protein of the human cytomegalovirus. 138 peptides were synthesized which cover the amino acid sequence of the whole protein (561 amino acids) to the full length thereof, neighboring peptides overlapping by 9 amino acids each. 138 is not a square number. The next higher square number from 138 is 144 (12×12). Thus, the peptides were distributed to 2×12, i.e. 24, groups in such a way that each peptide occurs in exactly two different groups. By combining the groups with positive results (stimulation), the stimulating peptide can be concluded directly (when only two groups show a positive result), or it can be narrowed down to a small number of candidate peptides which can be retested individually, if more then two groups of peptides have resulted in positive stimulation results. The principle of this grouping has been described in some detail by F. Kern et al., Journal of Virology, October 1999, p. 8179-8184. A possibility for telling by one single run with a corresponding negative control whether a protein has a stimulating effect on CD8+ T lymphocytes, i.e., whether the amino acid sequence of this protein contains epitopes which are recognized by CD8+ T lymphocytes, has not been described to date.

DESCRIPTION OF THE INVENTION

The object of the invention is to provide a possibility for how to employ protein antigens of known sequence for the immunostimulation of CD8+ and CD4+ T lymphocytes, wherein cellular antigen processing is not necessary and individual antigenic determinants (epitopes) need not be identified. It has now been found that a sufficient immunostimulation can be achieved by incubation with T lymphocytes of a special peptide library of individual fragments of the antigen with some overlapping of the fragments. The stimulation can be detected by flow cytometry. Thus, it can be established whether an organism (human or animal) has built up a T lymphocyte response against the immunizing antigen after an exposure which has occurred (also well-aimed immunization). This T lymphocyte reactivity can be examined in terms of its time course. A further object of the invention is to provide a method by which protein antigens whose amino acid sequences are known can be identified as T-lymphocyte-stimulating protein antigens within a short time and with comparably few expenditure. This further provides a possibility for examining prior to the selection of a protein for the identification of epitopes whether T-lymphocyte-stimulating antigenic determinants are at all present in this protein.

Thus, the present invention relates to
(1) a method for the antigen-specific stimulation of T lymphocytes with synthetic peptide libraries, comprising the following steps:
    (a) subdividing the total amino acid sequence of the antigen into protein fragments with partial amino acid sequences, wherein said protein fragments have a minimum length of 9 amino acid residues (also briefly referred to as "AA" in the following), and wherein adjacent or neighboring protein fragments are over-lapping with their partial amino acid sequence;
    (b) synthesizing a peptide library containing the protein fragments defined in (a);
    (c) incubating a suspension containing CD8+ and/or CD4+ T lymphocytes with all the protein fragments of the peptide library obtained in (b) in a single culture run;
(2) in a preferred embodiment of method (1), it is adapted for in-vivo and in-vitro immunostimulation of T lymphocytes of mammals, especially humans;
(3) stimulated T lymphocytes obtainable by the method as defined above under (2);
(4) use of a peptide library as defined above under (1) for the preparation of a medicament for in-vivo immunostimulation of T lymphocytes of mammals; and
(5) a composition for in-vitro and in-vivo immunostimulation of T lymphocytes of mammals, comprising one or more peptide libraries as defined above under (1).

DESCRIPTION OF FIGURES

FIG. 1: Peptides for whole pool HCMV IE-1 (laboratory strain AD169). The sequence of the starting protein, VIE1-HCMVA 55 kDa immediate-early protein 1 (IE1), human cytomegalovirus (strain AD169), is known from Swiss-Prot P13202 and depicted in SEQ ID NO:1.

FIG. 2: Peptides for whole pool HCMV pp65 (laboratory strain AD169). The sequence of the starting protein, PP65-HCMVA 65 kDa lower matrix phosphoprotein (pp65), human cytomegalovirus (strain AD169), is known from Swiss-Prot P06725 and depicted in SEQ ID NO:2.

DETAILED DESCRIPTION OF THE INVENTION

Figure 3:
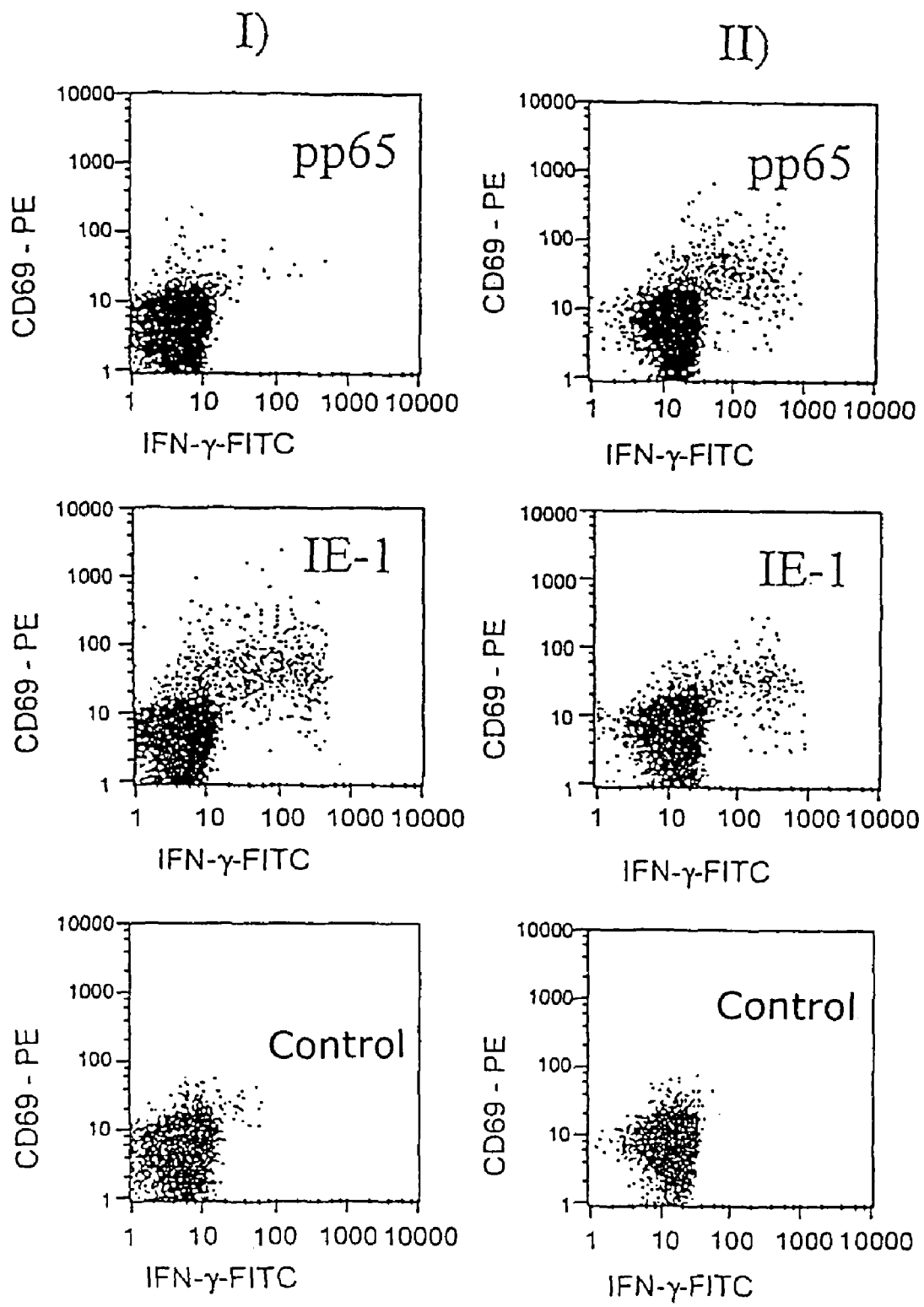
FIG. 3: Detection of intracellular interferon-gamma in CD8+ T lymphocytes upon stimulation with the peptide libraries described. The marker CD69 was used as an activation marker in addition to interferon-gamma. The representation has been limited to CD3+/CD8+ events, stating the average fluorescence intensity.

"Antigens" in the method according to the invention are those antigens which have a peptide basic structure (i.e., proteins, parts of proteins or polypeptides etc.). The antigen in step (a) of the above defined method is an antigen (i.e., protein, part of a protein, or polypeptide) to which a T lymphocyte stimulation is desired, or on which it is to be tested whether such a stimulation has already occurred.

"Proteins or peptides" in the present invention have a sequence of at least nine AAs as an essential feature.

A "peptide library" within the meaning of the application is a complex mixture of peptides which in their entirety cover the complete sequence of a protein antigen or partial antigen, which is in such a way that successive peptides are overlapping along this sequence.

Therefore, in the method according to embodiment (1) of the invention, it may be necessary to determine the total amino acid sequence of the antigen prior to the above mentioned step (a), especially when the amino acid sequence of the antigen is not known.

It does not matter how the sequence of the antigen has been established. Thus, for a new protein, the sequence can be analyzed for the first time, or for a known protein, it may be read from a data base. It is only important that the amino acid sequence of the protein or partial protein has been determined.

In a preferred embodiment of method (1) according to the invention, the protein fragments have a minimum length of 15 AAs and/or a maximum length of 35 AAs, preferably 25 AAs. It is further preferred that an overlap of 8 AAs, preferably 11 AAs, is present between neighboring protein fragments. In addition, the synthetic protein fragments may be extended by a maximum of 7 natural or artificial AAs and/or a protective group at either or both of their N terminus and C terminus. These extensions of natural or artificial AAs are non-overlapping sequences.

Suitable protective groups on the N terminus of the protein fragments are alkyl, aryl, alkylaryl, aralkyl, alkylcarbonyl or arylcarbonyl, having from 1 to 10 carbon atoms, an acyl group having from 1 to 7 carbon atoms, etc. Preferred protective groups for the N terminus are the naphthoyl, naphthylacetyl, naphthylpropionyl and benzoyl groups. Suitable protective groups for the C terminus of the protein fragments are alkoxy or aryloxy groups having from 1 to 10 carbon atoms or an amino group. Further protective groups are described in Houben-Weyl (1974), Georg Thieme Verlag, 4th Edition. The description of the protective groups in the above reference is included herein by reference.

Further, it is preferred that the concentration of the individual protein fragments of the peptide library is at least 1 ng/ml, preferably from about 0.1 to about 10 µg/ml in the culture run (final concentration). Particularly preferred is a concentration of about 1 µg/ml of culture broth.

In addition, it is preferred that the incubation solution (i.e., the culture broth) further contains one or more compounds having costimulatory properties, such as costimulatory antibodies (e.g. anti-CD28 or anti-CD49d) or other molecules having costimulatory properties. (e.g., stimulatory CTLA4-Ig). These compounds are preferably contained in the culture broth in final concentration of from 0.1 to 10 µg/ml.

A particularly preferred embodiment of the method (1) according to the invention for the antigen-specific stimulation of T lymphocytes with synthetic peptide libraries comprises the following steps:
    ($a_1$) determining the total amino acid sequence of the antigen, which is a protein or part of a protein;
    ($a_2$) subdividing the total amino acid sequence in protein fragments having partial amino acid sequences, wherein the protein fragments have a minimum length of 9 (preferably 15) AAs, optionally have a maximum length of 25 AAs, and wherein adjacent or neighboring protein fragments are over-lapping with their partial amino acid sequence, an overlap of 8 AAs, especially an overlap of 11 AAs, being preferred;
    (b) synthesizing a peptide library containing the protein fragments defined in (a2), optionally extended by a maximum of 7 natural or artificial amino acids and/or a protective group at either or both of the N terminus and C terminus;

(c) incubating a suspension containing CD8+ and/or CD4+ T lymphocytes with all the protein fragments of the peptide library in a single culture run.

Preferred is the use of the method according to the invention for identifying stimulating or non-stimulating mixtures of all protein fragments in a single culture run, wherein the following steps are added:

(d) identifying (preferably flow-cytometric identifying) of
  (i) at least one T-cell cytokine which was induced by the protein fragment or fragments and synthesized in the T lymphocytes, wherein said cytokine or cytokines are intracellular or bound to the cell membrane; and/or
  (ii) at least one activation marker which was induced by the protein fragment or fragments and synthesized in the T lymphocytes, wherein said activation marker or markers are intracellular or bound to the cell membrane.

The method (1) according to the invention is also suitable for establishing whether T-lymphocyte-stimulating antigenic determinants are present in an antigen.

The method according to the invention is further suitable for diagnostics, especially to establish whether a mammal, especially a human, has previously responded to a specific protein with its immune system, and how strong such response is.

According to the preferred embodiment (2) of the invention, the method is suitable for immunostimulation of T lymphocytes of mammals, especially humans, for both in-vitro and in-vivo applications. This method may further include the expanding of the stimulated T lymphocytes.

The above mentioned embodiments of the method according to the invention may also be designed to employ several different synthetic peptide libraries (from different antigens) together in one culture run or in separated culture runs.

Suspensions containing T lymphocytes within the meaning of this application are characterized by containing cells which can present MHC-bound peptides. Thus, the presenting cells may also be T lymphocytes in addition to the antigen-presenting cells.

An advantage of the method according to the invention is the fact that the identification of at least one T-cell cytokine or activation marker is effected on the level of the individual cell. Thus, it is possible to exactly determine the phenotype of the responding cells. Cytokines and surface markers are described in some detail in Abul K. Abbas et al. (1997), Cellular and Molecular Immunology, Philadelphia, 3rd Edition, ISBN 0-7216-4024-9.

It is known that protein fragments binding to MHC class I molecules (MHC=major histocompatibility complex) usually have a length of 9 amino acids, while protein fragments binding to MHC class II molecules are somewhat longer and more variable in length.

An advantage of methods (1) and (2) according to the invention is the fact that, despite of the short incubation time, the protein fragments are taken up by the MHC molecules present on the cell surface sufficiently to enable an unambiguous identification of a T-cell stimulation after six hours, for example.

In the method according to the invention, the suspension containing T lymphocytes can be derived from whole blood, peripheral white blood cells (PWBC), splenocytes, thymocytes, bone marrow, cerebrospinal fluid, lymph node cells, etc.

In the method according to the invention, it is particularly advantageous that processing of the T lymphocytes is not required. Thus, the T lymphocytes need not be enriched, and further, the removal or destruction of other cells is not necessary. Thus, the method according to the invention can be practiced more simply in a routine manner.

Preferred is a method according to the invention for antigen-specific stimulation of T lymphocytes with synthetic peptide libraries in which the suspension containing the T lymphocytes is derived from patients to be treated, from other donors or from animals. If the suspension containing T lymphocytes is derived from a patient, the identification can be used, for example, for establishing to which protein of a virus a CD8+ or CD4+ T lymphocyte response can be induced. The peptide library employed for examining this reactivity can then be selectively employed for the stimulation of further T lymphocytes of the same or other patients. The cells thus induced and stimulated for proliferation can be expanded in vivo or ex vivo and subsequently retransfused to the patient.

The method according to the invention can also be used in veterinary medicine. It is possible to use a wide variety of animal species and also constellations of animal patients and donors as the source of the suspension containing T lymphocytes.

Advantageous is a method according to the invention for the antigen-specific stimulation of T lymphocytes with synthetic peptide libraries in which the antigens, which are proteins or partial proteins, are derived from microorganisms, macroorganisms, cells, cell cultures and/or tissues from donors or patients. Microorganisms include, for example, viruses, bacteria, fungi, protozoans, parasites. Macroorganisms include, for example, all multicellular eukaryotes. This source is just important for influencing allergies. Included are animals and plants. There may be used cells, cell cultures or even whole tissues consisting of one or more layers or cell types.

Preferred is a method according to the invention for antigen-specific stimulation of T lymphocytes with synthetic peptide libraries in which the stimulation is detected by means of a flow cytometer. What is essential is the principle that markers present in the cell or on its surface, such as cytokines or surface markers, will contact with a specific detector, for example, an antibody, the detector being loaded with a fluorescent dye. Upon excitation by laser light of this fluorescent dye on the cells focused in a liquid stream, the flow cytometer records the emitted scattered light and fluorescence signals, which enables the simultaneous or later analysis of the cells. Such techniques are described in some detail in Howard M. Shapiro (1995), Practical Flow Cytometry, New York, 3rd Edition, ISBN 0-471-30376-3. The detection of the intracellular cytokines is described in I L L. Picker et al. (1995), Blood, Vol. 86, p. 1408.

The advantage of this method according to the invention for antigen-specific stimulation of T lymphocytes with synthetic peptide libraries is that a reagent for the immunostimulation of T lymphocytes can be made available within a very short period of time and, as compared to the conventional method, with very low expenditure. It is further advantageous that individual stimulating epitopes need not to be identified.

In a single run (one tube or one well or one flask, etc.), the T lymphocytes of a donor/patient (CD8 and/or CD4) can be stimulated simultaneously with all possible antigenic determinants of the protein (or proteins when several peptide libraries are used) without needing to be specifically known. For example, the T lymphocytes of a patient who has undergone a bone marrow transplantation could be incubated with HLA-identical dendritic cells which were previously incubated with such a mixture of peptides, and thus these T lymphocytes could be stimulated with all epitopes relevant (i.e., binding) to the particular HLA type without these epitopes needing to be known or becoming known by the method. The only critical point is that they stimulate T lymphocytes and belong to the selected protein or proteins. These cells could be retransferred to the patient within the scope of an adoptive immunotherapy.

A preferred source of the T lymphocytes to be stimulated are those (human or animal) donors which have previously build up an immunological primary response to the antigen or in which such an immune response to the antigen has been induced by exposure. This may have occurred, for example, within the scope of an infection or also within the scope of an immunization. This situation also prevails in an auto-immune response.

Another advantage is that the MHC type of the donor need not be known. A further advantage is that the stimulation of both CD8+ and CD4+ T lymphocytes can be examined simultaneously and in a single run.

The stimulated T lymphocytes according to embodiment (3) of the invention are preferably obtained by in-vitro stimulation. The stimulated lymphocytes are capable of being transfused into a patient.

The medicament according to embodiment (4) of the invention may contain further immunoreactive compounds, such as the above defined compounds having co-stimulating properties, in addition to usual additives and auxiliaries. The medicament may also contain several of the above defined peptide libraries.

The composition according to embodiment (5) can be a pharmaceutical composition, i.e., for the in-vivo treatment of humans and animals, or a diagnostic composition or a so-called kit, i.e., primary for in-vitro application, wherein the peptide library is respectively adapted to the antigen to be stimulated. As to further components of the composition, the same applies as has been set forth above with respect to embodiment (4).

The present invention is further illustrated by the following non-limiting Example.

EXAMPLE

Mononuclear cells were prepared from the peripheral blood of two patients obtained by venous puncture. The patients possessed antibodies against the human cytomegalovirus (HCMV). The cells prepared by standard methods were incubated for six hours under optimized conditions with peptide libraries for the HCMV proteins 65 kD lower matrix phosphoprotein (pp65) and 55 kDa immediate-early protein 1 (IE1). This is done according to the method described in Kern et al., Eur. J. Immunol. 30: 1676-1682 (2000), which comprises the following steps:

1. Resuspension of PBMC ($2.5 \times 10^6$/ml in RPMI 1640 with 2 mM glutamine added) after Ficoll preparation (standard protocol).
2. 400 µl of this suspension was mixed in an incubation vessel (sterile tube from Falcon No. 2054, 5 ml) with 100 µl of peptide solution (containing 10 µg of each individual peptide in RPMI 1640 with 2 mM glutamine added).
3. Incubation at 37° C. under an $H_2O$-saturated atmosphere with 5% $CO_2$ (standard incubator).
4. After 2 hours, there was added 500 µl of RPMI 1640 to which 20% fetal calf serum (v/v) and additionally glutamine (2 mM) and 10 µg of Brefeldin A (BFA, final concentration in the mix was 10 µg/ml) had been added. The final concentration of fetal calf serum in the mix is 10% (v/v). The final concentration of each individual peptide is 1 µg/ml. BFA serves to retain synthetic cytokines in the cells, which is of advantage for the detection of the intracellular cytokines. The final volume of the mix is 1 ml.
5. After further incubation for 4 h under the same conditions (i.e., a total incubation time of 6 h), the incubation was stopped by adding ice-cold PBS buffer solution.
6. This was followed by centrifugation (8 min, 400 g), decantation and further processing of the samples according to a standard protocol, including detachment from the tube wall using 2 mM EDTA/PBS solution, fixation, permeabilization and staining with monoclonal antibodies.
7. Analysis on a flow cytometer (e.g., a four-color fluorescence flow cytometer of the type FacsCalibur (Becton Dickinson)).

The sequences of IE-1 and pp65 have been deposited in the SWISS-PROT data base, European Bioinformatics Institute, under the Nos. P13202 (see also SEQ ID NO: 1) and P06725 (see also SEQ ID NO: 2). In addition, the sequences of both proteins are described in M. S. Chee, A. T. Bankier, S. Becks et al., Curr. Top. Microbiol. Immunol. 154: 125-169 (1990).

The peptide library which represents the 55 kD immediate-early protein 1 consisted of peptides of 15 amino acids length each with 9 overlaps between successive peptides (see FIG. 1), and the peptide library which represents the 65 kD lower matrix phosphoprotein consisted of peptides of 15 amino acids length each with 11 overlaps between successive peptides (see FIG. 2).

In two different individuals (columns "I)" and "II)" in FIG. 3), incubation with the peptide libraries resulted in the production of IFN-gamma in T cells, which was detected by measurement on a flow cytometer on the level of the individual cells (J. L. Picker et al. (1995), Blood, Vol. 86, p. 1408-1419), or else in no detectable stimulation. Individual I exhibited a CD8+ T lymphocyte response to IE-1, but not to pp65, whereas individual II exhibited a CD8+ T lymphocyte response to both proteins. Incubation with an irrelevant peptide did not produce this effect (control).

The invention claimed is:

1. A method for the human cytomegalovirus (HCMV) antigen-specific stimulation of T lymphocytes with a synthetic peptide library, said method comprising the following steps:

a) synthesizing a peptide library of an HCMV antigen, said HCVM antigen being a whole HCMV protein of known total amino acid sequence, wherein each of the peptides of said peptide library comprises an amino acid sequence that (i) is at least 15 amino acid residues in length, (ii) is a continuous fragment less than the entirety of said total amino acid sequence, and (iii) overlaps to an extent of at least 8 amino acids with the amino acid sequence of at least one other of said peptides; and wherein the amino acid sequences of the peptides in the peptide library span the total amino acid sequence of the whole HCMV protein;

b) incubating a T lymphocyte suspension comprising CD8+ T lymphocytes, CD4+ lymphocytes or a mixture of CD8+ T lymphocytes and CD4+ T lymphocytes with the peptide library in a single culture run; and c) identifying by flow-cytometry at least one result of said stimulating in b), wherein said at least one result is a release by said stimulated T lymphocytes of at least one T-cell cytokine and/or an expression by said stimulated T lymphocytes of at least one activation marker, wherein said release and expression are a result of said incubating of said T lymphocyte suspension with the peptide library in the single culture run.

2. The method according to claim 1, wherein the peptides have a minimum length of 15 AAs and a maximum length of 35 AAs.

3. The method according to claim 2, wherein the HCMV protein is selected from the group consisting of lower matrix phosphoprotein (pp65) and immediate-early protein 1 (1E1).

4. The method according to claim 2, wherein the peptides are extended by a maximum of 7 AAs and/or a protective group at either or both of their N terminus and C terminus.

5. The method according to claim 1, wherein the concentration of the individual peptides of the peptide library in the incubating suspension is at least 1 ng/ml.

6. The method according to claim 1, wherein at least one compound that co-stimulates T lymphocytes is added to the incubating suspension.

7. The method according to claim 1, wherein the total amino acid sequence of the protein is determined prior to step a) in the method.

8. The method according to claim 1, which further comprises determining whether T-lymphocyte-stimulating antigenic determinants are present in the protein.

9. The method according to claim 1, wherein the T lymphocytes are mammalian in origin.

10. The method according to claim 9, further comprising reproducing the stimulated T lymphocytes.

11. The method according to claim 1, wherein the peptides have a length of 25 AAs.

12. The method according to claim 1, wherein an overlap of 11 AAs exists between overlapping peptides.

13. The method according to claim 1, wherein the concentration of the individual peptides of the peptide library in the incubating suspension is 0.1 to 10 ug/ml.

* * * * *

UNITED STATES PATENT AND TRADEMARK OFFICE
CERTIFICATE OF CORRECTION

PATENT NO.         : 7,994,096 B2                                         Page 1 of 1
APPLICATION NO.    : 10/203915
DATED              : August 9, 2011
INVENTOR(S)        : Kern et al.

It is certified that error appears in the above-identified patent and that said Letters Patent is hereby corrected as shown below:

In the Claims

Column 105, line 6, "(1E1)" -- should read -- (IE1) --.

Signed and Sealed this
First Day of December, 2015

Michelle K. Lee
*Director of the United States Patent and Trademark Office*